United States Patent
Wu et al.

(10) Patent No.: US 11,513,044 B2
(45) Date of Patent: Nov. 29, 2022

(54) SPLIT-TYPE DEVICE FOR MEASURING ROCK MASS DEFORMATION UNDER HIGH HYDRAULIC PRESSURE AND CONSTRUCTION METHOD AND USE THEREOF

(71) Applicant: Changjiang River Scientific Research Institute of Changjiang Water Resources Commission, Hubei (CN)

(72) Inventors: Aiqing Wu, Hubei (CN); Lei Fan, Hubei (CN); Qixiang Fan, Hubei (CN); Xiaoyu Han, Hubei (CN); Zhiquan Ke, Hubei (CN); Yihu Zhang, Hubei (CN); Yuankun Liu, Hubei (CN); Zuowu Zhong, Hubei (CN); Meiwan Yu, Hubei (CN); Kun Wu, Hubei (CN); Wei Hu, Hubei (CN); Chong Chen, Hubei (CN); Qian Xiang, Hubei (CN)

(73) Assignee: Changjiang River Scientific Research Institute of Changjiang Water Resources Commission, Hubei (CN)

( * ) Notice: Subject to any disclaimer, the term of this patent is extended or adjusted under 35 U.S.C. 154(b) by 378 days.

(21) Appl. No.: 16/920,275

(22) Filed: Jul. 2, 2020

(65) Prior Publication Data
US 2021/0003489 A1  Jan. 7, 2021

(30) Foreign Application Priority Data
Jul. 3, 2019 (CN) .......................... 201910592026.2

(51) Int. Cl.
*G01N 3/06* (2006.01)
*G01N 3/10* (2006.01)
*G01N 3/62* (2006.01)
*G01N 33/24* (2006.01)

(52) U.S. Cl.
CPC ............... *G01N 3/066* (2013.01); *G01N 3/10* (2013.01); *G01N 3/62* (2013.01); *G01N 33/24* (2013.01)

(58) Field of Classification Search
CPC ........... G01N 3/066; G01N 3/10; G01N 3/62; G01N 33/24
USPC ......................................................... 73/768
See application file for complete search history.

(56) References Cited

FOREIGN PATENT DOCUMENTS

| CN | 205002729 | * | 1/2016 | |
| WO | WO-2022053073 A1 | * | 3/2022 | ............... G01B 7/02 |

* cited by examiner

*Primary Examiner* — Octavia Davis Hollington
(74) *Attorney, Agent, or Firm* — Nixon & Vanderhye P.C.

(57) ABSTRACT

A split-type device for measuring rock mass deformation under high hydraulic pressure and a construction method and use thereof. Main components of the device include a metal measuring rod, a magnetic iron core, a shell, a waterproof coil framework, a coil, a tail accessory, a cable clamp, a cable, a signal processing bin, etc. Main electronic components are treated by adopting the all-metal shell and a vacuum particle sealing double-layer sealing process, and have hydraulic pressure resistance of 5 MPa or above. Measurement signals feature centralized processing, digitization and dual utilization of signals, i.e., after data of a plurality of sensors is processed in an electronic bin and then digitized signals are connected to an independent reader outside the bin or a centralized acquisition device for in-situ tests.

16 Claims, 1 Drawing Sheet

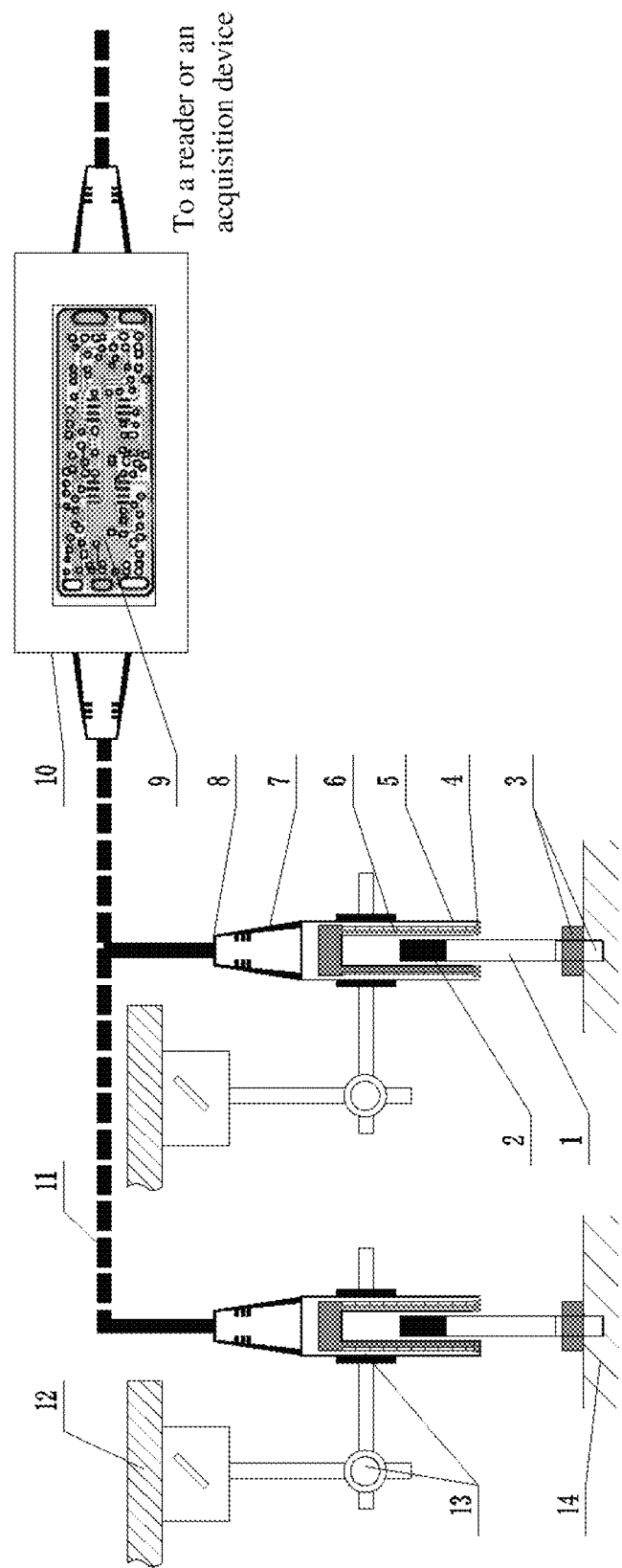

SPLIT-TYPE DEVICE FOR MEASURING ROCK MASS DEFORMATION UNDER HIGH HYDRAULIC PRESSURE AND CONSTRUCTION METHOD AND USE THEREOF

CROSS-REFERENCES TO RELATED APPLICATIONS

This application claims the benefit of Chinese Patent Application No. 201910592026.2, filed Jul. 3, 2019, the entire content of which is herein incorporated by reference.

STATEMENT REGARDING FEDERALLY SPONSORED RESEARCH OR DEVELOPMENT (Not Applicable)

TECHNICAL FIELD

The present invention belongs to the technical field of in-situ rock mass mechanics tests, and relates to a split-type device for measuring rock mass deformation under high hydraulic pressure during in-situ rock mass test and a construction method and use thereof.

BACKGROUND

In the in-situ test of rock mass, deformation strength parameters of rock mass are obtained by preparing samples on site and performing the load test. Since it is a large-scale in-situ test, the test results play an important role in engineering design. The in-situ test of rock mass is generally performed in a waterless exploratory adit. In the test, the deformation measurement of rock mass mainly uses a dial gage for artificial reading or an optical grating transducer for automatic acquisition.

In recent years, many high dam reservoirs have been designed and built in western China's water conservancy and hydropower projects, with the maximum dam height exceeding 300 m. Mechanical properties of large-size fractured rock mass under high hydraulic pressure and seepage need to be studied urgently. The in-situ test data is of great significance for the safe operation of dam foundation rock mass and reservoir bank slope rock mass. Therefore, technologies for in-situ test of fractured rock mass mechanics in a high hydraulic pressure environment are put forward, and the rock mass deformation measurement technology is mainly studied.

The novel rock mass mechanics in-situ test technology is implemented in a closed and narrow space in a high hydraulic pressure environment. The sensor installation space is small, manual reset cannot be performed for rock mass deformation measurement after a test cabin is closed, while test results need high-precision deformation data. In addition, the novel test technology has the overall requirements of digitalization and centralized automatic acquisition. Therefore, the measuring device needs to have a large range (20 cm) and high precision (μm level), be easy to digitize, bear high hydraulic pressure, and have small measurement components and high reliability.

SUMMARY

In view of the shortcomings in the prior art, the present invention provides a split-type device for measuring rock mass deformation under high hydraulic pressure and based on the principle of a linear variable differential transformer (LVDT) sensor and a preparation method thereof. The rock mass deformation measuring device can perfectly perform a deformation measuring task of a new rock mass mechanics in-situ test through split design and seal design of components by using friction-free measurement, high resolution and input/output isolation characteristics of the LVDT sensor.

The present invention provides the split-type device for measuring rock mass deformation under high hydraulic pressure, which occupies a narrow space and has high precision and digitalization. The split-type device for measuring rock mass deformation under high hydraulic pressure specifically includes a signal processing bin and one or more measuring units, where a circuit board is arranged in the signal processing bin, and the one or more measuring units are respectively in signal connection with the circuit board in the signal processing bin through a signal output cable; each of the measuring units includes a measuring bracket, a split measuring rod, a shell, a magnetic iron core, a non-magnetic coil framework and a coil wound around the non-magnetic coil framework, where the magnetic iron core is suspended in a center hole of the non-magnetic coil framework, one end of the magnetic iron core is connected to the measuring rod; the shell is wrapped outside the non-magnetic coil framework and the coil, a tail end of the shell is provided with a tail accessory and a cable clamp, the coil is sealed in the shell through the tail accessory, and the signal output cable is in signal connection with the coil in the shell through the tail accessory and the cable clamp; and the measuring bracket is connected onto the shell.

Further, when the measuring device is used to perform a rock mass deformation test, the measuring bracket of each of the measuring units is fixed at a fixed deformation measurement reference point selected in an in-situ rock mass test process, and one end, which is not connected to the magnetic iron core, of the measuring rod is fixed on a surface of a measured sample; the magnetic iron core is driven by the measuring rod to move axially to cut magnetic lines of force generated by the coil and generate a voltage difference, then a voltage change is demodulated and output to the circuit board inside the signal processing bin through the signal output cable, and an electric signal of the coil is digitally processed by the circuit board and then output to an external reader or a centralized data acquisition device.

Preferably, the non-magnetic coil framework has a cylindrical structure made of non-magnetic stainless steel (1Cr18Ni9Ti), a middle portion thereof is provided with a vertical center hole with a bottom opening, and the coil is wound around the non-magnetic coil framework, dipped in paint and dried; the shell is made of non-magnetic stainless steel (1Cr18Ni9Ti), an edge of the non-magnetic coil framework and the shell are coated and sealed by a vacuum particle sealing process to form a signal acquisition cavity, and the coil is sealed in the signal acquisition cavity formed between the non-magnetic coil framework and the shell.

Preferably, the measuring rod is made of non-magnetic stainless steel, and an end thereof not connected to the magnetic iron core is provided with a thread and a fastening nut.

Preferably, the signal processing bin is made of non-magnetic stainless steel, the circuit board is sealed in the signal processing bin, and both ends of the signal processing bin are respectively provided with tail accessories and cable clamps which are connected with cables.

Preferably, the measuring bracket is fixedly installed on the shell through a clamp.

Preferably, when the rock mass deformation test is performed, a measuring end of the measuring rod is buried below a surface of the measured sample and fixed by a fastening nut.

A method for constructing the split-type device for measuring rock mass deformation under high hydraulic pressure according to the present invention specifically includes the following steps:

step 1: manufacturing a waterproof non-magnetic coil framework by processing non-magnetic stainless steel, where the coil framework has a cylindrical structure, and a middle portion thereof is provided with a vertical center hole with a bottom opening; winding a coil around the waterproof coil framework, and then dipping the coil in paint and drying the coil;

step 2: sealing the waterproof non-magnetic coil framework prepared in step 1 by adopting an all-metal shell, installing a tail accessory and a cable clamp at a signal output end of the shell, and then coating and sealing the waterproof non-magnetic coil framework, the all-metal shell, the tail accessory and a cable clamp joint by a vacuum particle sealing process, so as to realize the overall water resistance and wear resistance of a sensor;

step 3: packaging a demodulator circuit board in the shell of a signal processing bin by a vacuum particle sealing process, and hermetically connecting a signal output cable of the demodulator circuit board with a signal output end of the waterproof non-magnetic coil framework;

step 4: vulcanizing the signal output cable, such that the vulcanized signal output cable passes a hydraulic pressure test to ensure that its hydraulic pressure resistance reaches 5 MPa;

step 5: manufacturing an independent measuring rod by using non-magnetic stainless steel, and connecting an end of the measuring rod to a magnetic iron core;

step 6: placing an end of the iron core of the split metal measuring rod in the vertical center hole of the sensor coil framework, and connecting a measuring unit main body to a measuring bracket; and step 7: calibrating linearity and accuracy of the manufactured measuring device, and testing hydraulic pressure resistance, where the performance test requirements are: displacement measuring range of 20 mm, linearity <0.05%, test resolution of 0.001 mm, hydraulic pressure resistance of 5 MPa, input working power of ±12 V DC (provided by a data acquisition instrument), rated displacement output signal: ±5 V DC, and the sensor with a pressure-resistant waterproof shielded cable of 5 m.

The present invention provides use of the split-type device for measuring rock mass deformation under high hydraulic pressure, where a rock mass deformation test is performed by using the split-type device for measuring rock mass deformation under high hydraulic pressure, specifically including the following steps:

(1) burying a non-magnetic stainless steel end of a split measuring rod of the measuring device in a surface of a measured rock mass sample, placing an end thereof connected to a magnetic iron core in a center hole of a non-magnetic coil framework, and fixing a measuring bracket at a fixed deformation measurement reference point selected in an in-situ rock mass test process; and (2) starting a loading control system for an in-situ rock mass hydraulic coupling test, performing a high hydraulic pressure-resistant in-situ rock mass test, cutting, through axial movement of the split iron core measuring rod, magnetic lines of force generated by the coil and generate a voltage difference, and measuring the voltage difference by a signal processing bin and then outputting the voltage difference through a cable.

Preferably, in step (1), an end of a non-magnetic iron core of the split measuring rod of the device is provided with an embedded thread and a fastening nut, buried below the surface of the measured rock mass sample, and connected by the fastening nut.

When the rock mass deformation test is performed in the present invention, the surface of the sample under deformation measurement is the surface of the rock mass sample, and the surface flatness and smoothness meet the requirements of relevant test procedures.

In the present invention, a framework is made of non-magnetic stainless steel (1Cr18Ni9Ti) and is in the form of blind holes, and then a coil is wound based on the framework, and after being tested to meet the requirements, the coil is dipped in paint under vacuum, and treatment is performed according to paint dipping regulations. After the process is completed, welding is performed. The shell and the framework are subjected to particle beam welding under vacuum, and a hydraulic pressure test is performed after it is confirmed that there is no problem with a welded joint, so as to ensure that the water resistance and pressure resistance meet the requirements. After the foregoing process is completed, debugging and an aging test are performed, then vacuum particle beam welding is performed again. A demodulator circuit is packaged into the shell, then a waterproof and pressure-resistant cable is vulcanized, and finally, the whole sensor output cable is placed into a water-tight cavity for a 6-7 MPa hydraulic pressure test. It is required to maintain the pressure for 2 h or above without pressure drop, so as to meet the requirement for hydraulic pressure resistance of 5 MPa.

In the present invention, the principle of an LVDT sensor is adopted for split and high hydraulic pressure resistance design of the measuring device. Main components of the device include a metal measuring rod, a shell, a waterproof coil framework, a tail accessory, a cable clamp, a cable, a signal processing bin, etc. Main electronic components are treated by adopting the all-metal shell and a vacuum particle sealing double-layer sealing process. The double-layer sealing treatment means that the main electronic components are sealed by the metal shell and a vacuum particle sealing process. After the main electronic components are sealed by the metal shell, all components except the cable are coated and sealed by physical and chemical means. The cable is of a high hydraulic pressure resistant type, so as to realize the overall water resistance of the deformation measuring device, and the reliable hydraulic pressure resistance is greater than 5 MPa. The coil and the circuit board in the signal processing bin are internal components of the sensor and are connected by a cable circuit. The magnetic iron core is suspended in the center hole of the sensor coil framework, and the magnetic lines of force generated by the coil are cut by axial movement and a voltage difference is generated, and then a voltage change is output through demodulation to truly reflect the deformation of a measured object. Electronic components, such as the circuit board, are arranged in the signal processing bin made of non-magnetic stainless steel. Measurement signals feature centralized processing, digitization and dual utilization of signals, i.e., after data of a plurality of sensors is processed in an electronic bin and then digitized signals are connected to an independent reader outside the bin or a centralized acquisition device for in-situ tests.

The waterproof coil framework and the all-metal shell wrap the coil to form a signal acquisition bin. The metal shell wraps and seals the internal coil and other components, and the shell is sealed against water and bears high hydraulic pressure, thus ensuring the normal operation of internal components in a high hydraulic pressure environment. An interface between the waterproof coil framework and the all-metal shell is coated and sealed by a vacuum particle sealing process, which realizes the overall water resistance and wear resistance of a deformation sensor signal acquisition bin. The waterproof coil framework is used for winding the coil to form a magnetic field. A main body of the waterproof coil framework is cylindrical, and forms a sealed space, namely a signal acquisition bin, together with the shell to protect the internal coil and other circuits. The tail accessory and the cable clamp are arranged at a tail end of a measuring component to protect the sensor signal output cable from water and pressure.

In the present invention, the iron core and the coil are separated from each other, and a non-magnetic waterproof coil framework is inserted between the iron core and an inner wall of the coil, so that high-pressure water or corrosive water can be isolated from the coil, the measuring rod does not need to be dynamically sealed any longer, and only the sensor coil needs to be hermetically sealed. The iron core and the sensor coil have a split structure, which does not cause friction, so the device has the advantages of high repeatability, fast dynamic response, long service life, etc. The signal acquisition bin composed of the waterproof coil framework, the coil and the all-metal shell is separated from the signal processing bin integrated with the circuit board, so that the sensor is installed in a narrow space of a sealed cabin of the in-situ hydraulic coupling test. The split iron core measuring rod designed in the present invention is not affected by the water environment, and is not in direct contact with the sensor coil and other parts. An end of the split iron core measuring rod is connected to the iron core, and is placed in the center hole of the sensor shell when working; and the other end is fixed on the surface of the measured sample by a nut when working.

The signal processing bin in the present invention is separated from an LVDT measurement component, which facilitates the installation of the measuring part in a closed and narrow space; a circuit board is arranged inside the signal processing bin, and can be connected to multiple sensor signals for centralized processing. Measurement results are digitized and then output to an external reader or a centralized data acquisition device by a cable. This component adopts a double-layer seal form of a metal shell and a vacuum particle seal, and can be placed far away from an acquisition site according to the test layout. Both ends of the signal processing bin are hermetically connected to cables through tail accessories and cable clamps, which can protect an interface of a sensor signal transmission cable from water and pressure. The signal processing bin performs A/D conversion on measured data and outputs the measured data to the outside, thus realizing the digital upgrade of the measured data. Digital transmission processing reduces the voltage loss in long circuit transmission of analog signals and improves the measurement accuracy of the device. The signal dual utilization features that an outlet cable of the signal processing bin can be connected to a separate external reader or a centralized acquisition device for in-situ test to provide matched digitized signals.

The present invention breaks through the limitation that the deformation measurement cannot be performed in the conventional in-situ rock mass test under a hydraulic pressure, and solves the deformation test problem of the in-situ rock mass test under a high hydraulic pressure. The present invention realizes the upgrading and transformation from conventional manual recording to digital data transmission, real-time viewing and acquisition, can provide basic data for the design and stability evaluation of a high dam foundation, a hydrous slope and an underground cavern, and provides an effective and reliable means for the research of hydraulic coupling deformation strength characteristics of engineering rock mass in a complex environment.

The present invention breaks through the limitation that deformation measurement cannot be performed in the conventional in-situ rock mass test under a hydraulic pressure, a digital and split deformation measuring device resistant to a high hydraulic pressure is implemented by adopting the principle of a differential transformer sensor. The device features high hydraulic pressure resistance, anti-interference, high precision, high resolution, suitability for overall test requirements, etc., and has the advantages of high repeatability, fast dynamic response, long service life, etc. The device can ensure accurate and true measurement of deformation strength parameter indexes of underwater rock mass.

BRIEF DESCRIPTION OF THE DRAWINGS

FIG. 1 is a schematic structural diagram of the present invention.

1. measuring rod, 2. magnetic iron core, 3. thread and fastening nut, 4. non-magnetic coil framework, 5. shell, 6. coil, 7. tail accessory, 8. cable clamp, 9. circuit board, 10. signal processing bin, 11. signal output cable, 12. deformation measurement reference point, 13. measuring bracket, 14. measured sample.

DETAILED DESCRIPTION

The present invention will be further described in detail with reference to the accompanying drawings and specific examples. The examples are specifically shown in FIG. 1. The following detailed description of the examples of the present invention provided in the accompanying drawings is not intended to limit the scope of the claimed present invention, but merely represents selected examples of the present invention. All other examples obtained by a person of ordinary skill in the art based on the examples of the present invention without creative efforts shall fall within the protection scope of the present invention.

In the description of the present invention, it should be understood that orientation or position relationships indicated by terms "upper", "lower", "inner", "outer", "left", "right", etc. are orientation or position relationships shown in the accompanying drawings, or the usual orientation or position relationships of the products of the present invention when in use, or orientation or position relationships commonly understood by those skilled in the art. These terms are only used to facilitate description of the present invention and simplify the description, but not to indicate or imply that the mentioned device or components must have a specific orientation or must be established and operated in a specific orientation, and thus these terms cannot be understood as a limitation to the present invention.

A split-type device for measuring rock mass deformation under high hydraulic pressure provided by the example is specifically shown in FIG. 1. The measuring device includes a signal processing bin 10 and a plurality of measuring units, where the signal processing bin 10 is made of non-magnetic stainless steel, and a circuit board 9 is arranged in the signal processing bin 10. The circuit board 9 is sealed in the signal processing bin 10, and both ends of the signal processing bin 10 are respectively provided with tail accessories and cable clamps which are connected with cables. Both ends of the signal processing bin 10 are hermetically connected to the cables through the tail accessories and the cable clamps, which can protect an interface of a sensor signal transmission cable from water and pressure. The plurality of measuring units are in signal connection with the circuit board 9 in the signal processing bin 10 respectively through signal output cables 11.

As shown in FIG. 1, each of the measuring units includes a measuring bracket 13, a shell 5, a split measuring rod 1, a magnetic iron core 2, a non-magnetic coil framework 4 and a coil 6 wound around the non-magnetic coil framework 4. The non-magnetic coil framework 4 has a cylindrical structure made of non-magnetic stainless steel and is used for winding the coil to form a magnetic field, and a middle portion of the non-magnetic coil framework is provided with a vertical center hole with a bottom opening. The coil 6 is wound around the non-magnetic coil framework 4, dipped in paint and dried. The shell 5 is made of non-magnetic stainless steel, and the shell 5 is wrapped outside the non-magnetic coil framework 4 and the coil 6. A tail end of the shell 5 is provided with a tail accessory 7 and a cable clamp 8. An edge of the non-magnetic coil framework 4 and the shell 5 are coated and sealed by a vacuum particle sealing process to form a signal acquisition cavity, so as to realize the overall water resistance and wear resistance of the deformation sensor signal acquisition bin. The coil 6 is sealed in the signal acquisition cavity formed between the non-magnetic coil framework 4 and the shell 5. A signal output end of the coil 6 is in signal connection with the circuit board 9 in the signal processing bin 10 through a signal output cable 11. The measuring bracket 13 is fixedly installed on the shell 5 through a clamp. The measuring rod 1 is made of non-magnetic stainless steel, one end thereof is connected to the magnetic iron core 2 suspended in the center hole of the non-magnetic coil framework 4, and the other end is provided with a thread and a fastening nut 3 which are fixedly connected to the surface of the measured sample 14.

As shown in FIG. 1, when the measuring device in the present invention is used to perform a rock mass deformation test, the measuring bracket 13 of each of the measuring units is fixed at a fixed deformation measurement reference point 12 selected in an in-situ rock mass test process, and one end, which is not connected to the magnetic iron core 2, of the measuring rod 1 is fixed on a surface of a measured sample 14; the magnetic iron core 2 is driven by the measuring rod 1 to move axially to cut magnetic lines of force generated by the coil 6 and generate a voltage difference, then a voltage change is demodulated and output to the circuit board 9 inside the signal processing bin 10 through the signal output cable 11, and an electric signal of the coil 6 is digitally processed by the circuit board 9 and then output to an external reader or a centralized data acquisition device, to truly reflect the deformation of a measured object. A measuring end of the measuring rod 1 is buried below a surface of the measured sample 14 and fixed by a fastening nut. The deformation measurement reference point 12 is a fixed point selected during the in-situ test of rock mass, and the deformation measurement reference point 12 has no deformation during the test. The surface flatness and smoothness of the measured sample 14 meet the requirements of relevant test regulations.

The specific construction process of the measuring device in the example includes the following steps.

Step 1: Manufacture a waterproof non-magnetic coil framework 4 by processing non-magnetic stainless steel (1Cr18Ni9Ti), where the coil framework has a cylindrical structure, and a middle portion thereof is provided with a vertical center hole with a bottom opening; wind a coil 6 around the waterproof coil framework, and then dip the coil in paint and dry the coil.

Step 2: Seal the waterproof non-magnetic coil framework 4 prepared in step 1 by adopting an all-metal shell 5, install a tail accessory 7 and a cable clamp 8 at a signal output end of the shell, connect a signal output end through a cable, then coat and seal the waterproof non-magnetic coil framework 4, the all-metal shell 5, the tail accessory 7 and a joint of the cable clamp 8 by a vacuum particle sealing process, perform a hydraulic pressure test on an interface of a signal transmission cable after it is confirmed that there is no problem with a welded joint, so as to ensure that the water resistance and pressure resistance meet the requirements; and then debug the coil framework and perform an aging test to realize the overall water resistance and wear resistance of a sensor.

Step 3: Manufacture a demodulator circuit board 9, place the circuit board in a signal processing bin 10 made of non-magnetic stainless steel (1Cr18Ni9Ti), package the demodulator circuit board 9 in the shell of the signal processing bin 10 by a vacuum particle sealing technology, and install cable tail accessories and cable clamps at both ends of the signal processing bin, where signal output cables 11 at both ends of the demodulator circuit board 9 respectively extend out from the cable tail accessories and cable clamps at both ends of the signal processing bin.

Step 4: Connect the signal output cables 11 in step (3) with cables of the waterproof non-magnetic coil framework 4 at the signal output ends of the tail accessories 7 and the cable clamps 8.

Step 5: Vulcanize the signal output cables 11, and place the whole sensor output cable into a water-tight cavity for a 6-7 MPa hydraulic pressure test, where it is required to maintain the pressure for 2 h or above without pressure drop, so as to meet the requirement for hydraulic pressure resistance of 5 MPa.

Step 6: Manufacture an independent measuring rod 1 by using non-magnetic stainless steel (1Cr18Ni9Ti), and connect an end of the measuring rod 1 to a magnetic iron core 2.

Step 7: Place an end of the iron core of the split metal measuring rod in the vertical center hole of the sensor coil framework, and connect a measuring unit main body to a measuring bracket 13.

Step 8: Calibrate linearity and accuracy of the manufactured measuring device, and test hydraulic pressure resistance, where the performance test requirements are: displacement measuring range of 20 mm, linearity <0.05%, test resolution of 0.001 mm, hydraulic pressure resistance of 5 MPa, input working power of ±12 V DC (provided by a data acquisition instrument), rated displacement output signal: ±5 V DC, and the sensor with a pressure-resistant waterproof shielded cable of 5 m.

When the split-type device for measuring rock mass deformation under high hydraulic pressure in the present invention is specifically used, a non-magnetic stainless steel end, namely a measuring rod sample end 3, of a split metal measuring rod 1 is buried in a surface of a rock mass sample 14, an end of a magnetic iron core 2 is placed in a center hole of a non-magnetic coil framework 4 of a measuring unit, and a measuring unit main body is fixed on an in-situ rock mass test measuring bracket 13. A loading control system for an in-situ rock mass hydraulic coupling test is started, and a high hydraulic pressure-resistant in-situ rock mass test is performed. Magnetic lines of force generated by a coil 6 are cut through axial movement of the split iron core measuring rod 1 and a voltage difference is generated. The voltage difference is measured by a signal processing bin 10 and then output through a cable 11, demodulated and then recorded by computer software, to truly reflect the deformation of a measured object.

In the present invention, the magnetic iron core 2 and the coil 6 are separated from each other, and a non-magnetic waterproof framework is inserted between the iron core 2 and an inner wall of the coil 6, so that high-pressure water or corrosive water can be isolated from a coil assembly, the split measuring rod as a movement component does not need to be dynamically sealed any longer, and only the sensor coil needs to be hermetically sealed. The magnetic iron core 2 and a measuring unit main body have a split structure, which does not cause friction, so the device has the advantages of high repeatability, fast dynamic response, long service life, etc. The signal acquisition bin composed of the waterproof non-magnetic coil framework 4, the coil 6 and the all-metal shell 5 is separated from the signal processing bin 10 integrated with the circuit board, so that the sensor is installed in a narrow space of a sealed cabin of the in-situ hydraulic coupling test. The present invention can bear an external high hydraulic pressure as a whole.

The above is merely an example of the present invention, and the description thereof is more specific and detailed, but should not be construed as limiting the scope of the present invention. It should be noted that those of ordinary skill in the art can further make several variations and improvements without departing from the idea of the present invention. These all fall within the protection scope of the present invention. Therefore, the protection scope of the present invention should be subject to the appended claims.

The invention claimed is:

1. A split-type device for measuring rock mass deformation under high hydraulic pressure, comprising a signal processing bin and one or more measuring units, wherein a circuit board is arranged in the signal processing bin, and the one or more measuring units are respectively in signal connection with the circuit board in the signal processing bin through a signal output cable; each of the measuring units comprises a measuring bracket, a shell, a split measuring rod, a magnetic iron core, a non-magnetic coil framework and a coil wound around the non-magnetic coil framework, wherein the magnetic iron core is suspended in a center hole of the non-magnetic coil framework, one end of the magnetic iron core is connected to the measuring rod; the shell is wrapped outside the non-magnetic coil framework and the coil, a tail end of the shell is provided with a tail accessory and a cable clamp, the coil is sealed in the shell through the tail accessory, and the signal output cable is in signal connection with the coil in the shell through the tail accessory and the cable clamp; and the measuring bracket is connected onto the shell.

2. The split-type device for measuring rock mass deformation under high hydraulic pressure according to claim 1, wherein when the measuring device is used to perform a rock mass deformation test, the measuring bracket of each of the measuring units is fixed at a fixed deformation measurement reference point selected in an in-situ rock mass test process, and one end, which is not connected to the magnetic iron core, of the measuring rod is fixed on a surface of a measured sample; the magnetic iron core is driven by the measuring rod to move axially to cut magnetic lines of force generated by the coil and generate a voltage difference, then a voltage change is demodulated and output to the circuit board inside the signal processing bin through the signal output cable, and an electric signal of the coil is digitally processed by the circuit board and then output to an external reader or a centralized data acquisition device.

3. The split-type device for measuring rock mass deformation under high hydraulic pressure according to claim 2, wherein the non-magnetic coil framework has a cylindrical structure made of non-magnetic stainless steel, a middle portion thereof is provided with a vertical center hole with a bottom opening, and the coil is wound around the non-magnetic coil framework, dipped in paint and dried; the shell is made of non-magnetic stainless steel, an edge of the non-magnetic coil framework and the shell are coated and sealed by a vacuum particle sealing process to form a signal acquisition cavity, and the coil is sealed in the signal acquisition cavity formed between the non-magnetic coil framework and the shell.

4. The split-type device for measuring rock mass deformation under high hydraulic pressure according to claim 2, wherein the measuring rod is made of non-magnetic stainless steel, and an end thereof not connected to the magnetic iron core is provided with a thread and a fastening nut.

5. The split-type device for measuring rock mass deformation under high hydraulic pressure according to claim 2, wherein the signal processing bin is made of non-magnetic stainless steel, the circuit board is sealed in the signal processing bin, and both ends of the signal processing bin are respectively provided with tail accessories and cable clamps which are connected with a cable.

6. The split-type device for measuring rock mass deformation under high hydraulic pressure according to claim 2, wherein the measuring bracket is fixedly installed on the shell through a clamp.

7. The split-type device for measuring rock mass deformation under high hydraulic pressure according to claim 2, wherein when the rock mass deformation test is performed, a measuring end of the measuring rod is buried below a surface of the measured sample and fixed by a fastening nut.

8. The split-type device for measuring rock mass deformation under high hydraulic pressure according to claim 1, wherein the non-magnetic coil framework has a cylindrical structure made of non-magnetic stainless steel, a middle portion thereof is provided with a vertical center hole with a bottom opening, and the coil is wound around the non-magnetic coil framework, dipped in paint and dried; the shell is made of non-magnetic stainless steel, an edge of the non-magnetic coil framework and the shell are coated and sealed by a vacuum particle sealing process to form a signal acquisition cavity, and the coil is sealed in the signal acquisition cavity formed between the non-magnetic coil framework and the shell.

9. The split-type device for measuring rock mass deformation under high hydraulic pressure according to claim 1, wherein the measuring rod is made of non-magnetic stainless steel, and an end thereof not connected to the magnetic iron core is provided with a thread and a fastening nut.

10. The split-type device for measuring rock mass deformation under high hydraulic pressure according to claim 1, wherein the signal processing bin is made of non-magnetic stainless steel, the circuit board is sealed in the signal processing bin, and both ends of the signal processing bin are respectively provided with tail accessories and cable clamps which are connected with a cable.

11. The split-type device for measuring rock mass deformation under high hydraulic pressure according to claim 1, wherein the measuring bracket is fixedly installed on the shell through a clamp.

12. A method for constructing the split-type device for measuring rock mass deformation under high hydraulic pressure according to claim 1, specifically comprising the following steps:
step 1: manufacturing a waterproof non-magnetic coil framework by processing non-magnetic stainless steel, wherein the coil framework has a cylindrical structure, and a middle portion thereof is provided with a vertical center hole with a bottom opening; winding a coil around the waterproof coil framework, and then dipping the coil in paint and drying the coil;
step 2: sealing the waterproof non-magnetic coil framework prepared in step 1 by adopting an all-metal shell, installing a tail accessory and a cable clamp at a signal output end of the shell, and then coating and sealing the waterproof non-magnetic coil framework, the all-metal shell, the tail accessory and a cable clamp joint by a vacuum particle sealing process, so as to realize the overall water resistance and wear resistance of a sensor;
step 3: packaging a demodulator circuit board in the shell of a signal processing bin by a vacuum particle sealing process, and hermetically connecting a signal output cable of the demodulator circuit board with a signal output end of the waterproof non-magnetic coil framework;
step 4: vulcanizing the signal output cable, such that the vulcanized signal output cable passes a hydraulic pressure test to ensure that its hydraulic pressure resistance reaches 5 MPa;
step 5: manufacturing an independent measuring rod by using non-magnetic stainless steel, and connecting an end of the measuring rod to a magnetic iron core;
step 6: placing an end of the iron core of the split metal measuring rod in the vertical center hole of the sensor coil framework, and connecting a measuring unit main body to a measuring bracket; and
step 7: calibrating linearity and accuracy of the manufactured measuring device, and testing hydraulic pressure resistance, wherein the performance test requirements are: displacement measuring range of 20 mm, linearity <0.05%, test resolution of 0.001 mm, hydraulic pressure resistance of 5 MPa, input working power of ±12 V DC, rated displacement output signal: ±5 V DC, and the sensor with a pressure-resistant waterproof shielded cable of 5 m.

13. Use of the split-type device for measuring rock mass deformation under high hydraulic pressure according to claim 12, wherein a rock mass deformation test is performed by using the split-type device for measuring rock mass deformation under high hydraulic pressure, specifically comprising the following steps:
(1) burying a non-magnetic stainless steel end of a split measuring rod of the measuring device in a surface of a measured rock mass sample, placing an end thereof connected to a magnetic iron core in a center hole of a non-magnetic coil framework, and fixing a measuring bracket at a fixed deformation measurement reference point selected in an in-situ rock mass test process; and
(2) starting a loading control system for an in-situ rock mass hydraulic coupling test, performing an in-situ high hydraulic pressure-resistant rock mass test, cutting, through axial movement of the split iron core measuring rod, magnetic lines of force generated by the coil and generate a voltage difference, and measuring the voltage difference by a signal processing bin and then outputting the voltage difference through a cable.

14. The use of the split-type device for measuring rock mass deformation under high hydraulic pressure according to claim 13, wherein in step (1), an end of a non-magnetic iron core of the split measuring rod of the device is provided with an embedded thread and a fastening nut, buried below the surface of the measured rock mass sample, and connected by the fastening nut.

15. Use of the split-type device for measuring rock mass deformation under high hydraulic pressure according to claim 1, wherein a rock mass deformation test is performed by using the split-type device for measuring rock mass deformation under high hydraulic pressure, specifically comprising the following steps:
(1) burying a non-magnetic stainless steel end of a split measuring rod of the measuring device in a surface of a measured rock mass sample, placing an end thereof connected to a magnetic iron core in a center hole of a non-magnetic coil framework, and fixing a measuring bracket at a fixed deformation measurement reference point selected in an in-situ rock mass test process; and
(2) starting a loading control system for an in-situ rock mass hydraulic coupling test, performing an in-situ high hydraulic pressure-resistant rock mass test, cutting, through axial movement of the split iron core measuring rod, magnetic lines of force generated by the coil and generate a voltage difference, and measuring the voltage difference by a signal processing bin and then outputting the voltage difference through a cable.

16. The use of the split-type device for measuring rock mass deformation under high hydraulic pressure according to claim 15, wherein in step (1), an end of a non-magnetic iron core of the split measuring rod of the device is provided with an embedded thread and a fastening nut, buried below the surface of the measured rock mass sample, and connected by the fastening nut.

* * * * *